US009345743B2

(12) United States Patent
Oda et al.

(10) Patent No.: US 9,345,743 B2
(45) Date of Patent: May 24, 2016

(54) AGENT FOR PROMOTING PROLIFERATION OF BIFIDOBACTERIA

(75) Inventors: Hirotsugu Oda, Kanagawa (JP); Koji Yamauchi, Kanagawa (JP); Takumi Sato, Kanagawa (JP); Kanetada Shimizu, Kanagawa (JP)

(73) Assignee: MORINAGA MILK INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 14/346,050

(22) PCT Filed: Aug. 24, 2012

(86) PCT No.: PCT/JP2012/071443
§ 371 (c)(1),
(2), (4) Date: Mar. 20, 2014

(87) PCT Pub. No.: WO2013/094250
PCT Pub. Date: Jun. 27, 2013

(65) Prior Publication Data
US 2015/0139955 A1     May 21, 2015

(30) Foreign Application Priority Data
Dec. 19, 2011   (JP) ................ 2011-277081

(51) Int. Cl.
| | |
|---|---|
| A61K 38/40 | (2006.01) |
| A61K 38/10 | (2006.01) |
| C07K 14/79 | (2006.01) |
| A23L 1/30 | (2006.01) |
| A61K 35/745 | (2015.01) |
| A23L 1/305 | (2006.01) |
| A23L 2/52 | (2006.01) |
| A61K 35/74 | (2015.01) |
| C07K 7/08 | (2006.01) |

(52) U.S. Cl.
CPC .............. *A61K 38/10* (2013.01); *A23L 1/3014* (2013.01); *A23L 1/3053* (2013.01); *A23L 2/52* (2013.01); *A61K 35/74* (2013.01); *A61K 35/745* (2013.01); *A61K 38/40* (2013.01); *C07K 7/08* (2013.01); *C07K 14/79* (2013.01); *A23V 2002/00* (2013.01); *A23Y 2300/29* (2013.01); *A23Y 2300/45* (2013.01)

(58) Field of Classification Search
None
See application file for complete search history.

(56) References Cited

U.S. PATENT DOCUMENTS

| | | | |
|---|---|---|---|
| 6,849,593 B1 | 2/2005 | Forssmann et al. | |
| 2009/0270309 A1* | 10/2009 | Cornish | A61K 38/40 514/1.1 |

FOREIGN PATENT DOCUMENTS

| | | |
|---|---|---|
| JP | 07-267866 | 10/1995 |
| JP | 2001-516570 A | 10/2001 |
| JP | 2003-171399 A | 6/2003 |

OTHER PUBLICATIONS

Hoek et al., "Antibacterial Activity of Bovine Lactoferrin-Derived Peptides", Antimicrobial Agents and Chemotherapy, Jan. 1997, p. 54-59.*
Tomito et al., "Antimicrobial Peptides of Lactoferrin", Lactoferrin: Structure and Function, 1994; pp. 209-218.*
Ishibashi et al., "Probiotics and safety", The American Journal of Clinical Nutrition, 2001, pp. 465S-470S.*
Bernet et al., "Adhesion of Human Biofidobacterial Strains to Cultured Human Intestinal Epithelial Cells and Inhibition of Enteropathogen-Cell Interactions", Applied and Environmental Microbiology, 1993, pp. 4121-4128.*
Extended European Search Report for European Patent Application No. 12858857.1, issued on May 18, 2015.
Rahman et al., "Growth promotion and cell binding ability of bovine lactoferrin to Bifidobacterium longum," Anaerobe, vol. 15(4), pp. 133-137 (2009).
Azuma et al., "Bifidus Growth-promoting Activity of a Glycomacropeptide Derived from Human K-Casein," Agric. Biol. Chem., vol. 48(8), pp. 2159-2162 (1984).
Dionysius et al., "Antibacterial Peptides of Bovine Lactoferrin: Purification and Characterization," Journal of Dairy Science, vol. 80(4), pp. 667-674 (1997).
Kim et al., "Growth-promoting effects of lactoferrin on L. acidophilus and Bifidobacterium spp.," BioMetals, vol. 17, pp. 279-283 (2004).
Kim et al., "Comparison of Growth Promoting Effects on Bifidobacterium spp. by Bovine Lactoferrin Hydrolysates," Bioscience Microflora, vol. 24(4), pp. 119-123 (2005).
Liepke et al., "Human milk provides peptides highly stimulating the growth of bifidobacteria," Eur. J. Biochem., vol. 269, pp. 712-718 (2002).
Mitsuoka, "Human Microbiota Research—Present and Future," Journal of Intestinal Microbiology, vol. 19, pp. 179-192 (2005).
Petschow et al., "Ability of lactoferrin to promote the growth of Bifidobacterium spp. in vitro is independent of receptor binding capacity and iron saturation level," J. Med. Microbiol., vol. 48, pp. 541-549 (1999).
Rahman et al., "Growth Promotional Effects of Bovine Lactoferrin and its Hydrolysate on Bifidobacteria," Milk Science, vol. 53(4), pp. 325-327 (2004).
Rahman et al., "Screening of Bifidobacterium spp. based on in vitro growth responses to bovine lactoferrin," International Journal of Food, Science and Technology, vol. 45, pp. 453-458 (2010).

* cited by examiner

*Primary Examiner* — Lianko Garyu
(74) *Attorney, Agent, or Firm* — Knobbe, Martens, Olson & Bear, LLP

(57) ABSTRACT

A peptide dimer comprising a peptide consisting of the amino acid sequence of SEQ ID NO: 1 and a peptide consisting of any one of the amino acid sequences of SEQ ID NOS: 2 to 4, wherein the peptide consisting of the amino acid sequence of SEQ ID NO: 1 and the peptide consisting of any one of the amino acid sequences of SEQ ID NOS: 2 to 4 are bound through a disulfide bond between a cysteine residue of each peptide is used as an active ingredient of an agent for promoting proliferation of one or more bacterium selected from the group consisting of Bifidobacterium infantis and Bifidobacterium breve.

5 Claims, No Drawings

SEQUENCE LISTING

```
<160> NUMBER OF SEQ ID NOS: 5

<210> SEQ ID NO 1
<211> LENGTH: 16
<212> TYPE: PRT
<213> ORGANISM: Artificial Sequence
<220> FEATURE:
<223> OTHER INFORMATION: partial peptide of bovine lactoferrin

<400> SEQUENCE: 1

Ala Pro Arg Lys Asn Val Arg Trp Cys Thr Ile Ser Gln Pro Glu Trp
1               5                   10                  15

<210> SEQ ID NO 2
<211> LENGTH: 6
<212> TYPE: PRT
<213> ORGANISM: Artificial Sequence
<220> FEATURE:
<223> OTHER INFORMATION: partial peptide of bovine lactoferrin

<400> SEQUENCE: 2

Leu Glu Cys Ile Arg Ala
1               5

<210> SEQ ID NO 3
<211> LENGTH: 5
<212> TYPE: PRT
<213> ORGANISM: Artificial Sequence
<220> FEATURE:
<223> OTHER INFORMATION: partial peptide of bovine lactoferrin

<400> SEQUENCE: 3

Glu Cys Ile Arg Ala
1               5

<210> SEQ ID NO 4
<211> LENGTH: 4
<212> TYPE: PRT
<213> ORGANISM: Artificial Sequence
<220> FEATURE:
<223> OTHER INFORMATION: partial peptide of bovine lactoferrin
```

```
<400> SEQUENCE: 4

Cys Ile Arg Ala
1

<210> SEQ ID NO 5
<211> LENGTH: 49
<212> TYPE: PRT
<213> ORGANISM: Artificial Sequence
<220> FEATURE:
<223> OTHER INFORMATION: partial peptide of human lactoferrin

<400> SEQUENCE: 5

Gly Arg Arg Arg Arg Ser Val Gln Trp Cys Ala Val Ser Gln Pro Glu
1               5                   10                  15

Ala Thr Lys Cys Phe Gln Trp Gln Arg Asn Met Arg Lys Val Arg Gly
            20                  25                  30

Pro Pro Val Ser Cys Ile Lys Arg Asp Ser Pro Ile Gln Cys Ile Gln
        35                  40                  45

Ala
```

AGENT FOR PROMOTING PROLIFERATION OF BIFIDOBACTERIA

CROSS-REFERENCE TO RELATED APPLICATIONS

This application is the U.S. National Phase under 35 U.S.C. §371 of International Application PCT/JP2012/071443, filed Aug. 24, 2012, which was published in a non-English language, which claims priority to JP Application No. 2011-277081, filed Dec. 19, 2011.

Reference to Sequence Listing

This application incorporates by reference the sequence listing submitted as ASCII text filed via EFS-Web on Mar. 20, 2014. The Sequence Listing is provided as a file entitled "seqlst toya108.036apc," created on Mar. 19, 2014, and which is approximately 2 kilobytes in size.

TECHNICAL FIELD

The present invention relates to an agent for promoting proliferation of bifidobacteria, especially *Bifidobacterium infantis* and *Bifidobacterium breve*. The proliferation promoting agent of the present invention can be used for food, feed or drug.

BACKGROUND ART

It is known that *bifidobacteria* (bacteria belonging to the genus *Bifidobacterium*) are most dominant in the intestinal bacterial flora of infants, and it is considered that this fact closely relates to maintenance of health of infants. The pattern of *bifidobacteria* species living in human intestines changes with aging. The pattern is mainly constituted by *Bifidobacterium infantis* and *Bifidobacterium breve* in infancy, and is mainly constituted by *Bifidobacterium longum* and *Bifidobacterium adolescentis* in adulthood (Non-patent document 1). Therefore, for maintenance of infants' health, it is an important object to develop foodstuffs that promote proliferation of especially *Bifidobacterium infantis* and *Bifidobacterium breve* among the *bifidobacteria*.

As a *bifidobacterium* proliferation promoting substance, lactoferrin is known among milk proteins (Non-patent document 2), and bovine lactoferrin is widely used for powdered milk for child care, supplements, and so forth.

Further, as peptides obtained by enzymatic digestion of milk proteins, casein glycomacropeptides (Non-patent document 3) and human lactoferrin peptides (Non-patent document 4) are known. It has been reported that the human lactoferrin peptides are bifidogenic (a property of promoting proliferation of *bifidobacteria*) for *Bifidobacterium bifidum* (Patent document 1). However, although *Bifidobacterium bifidum* is detected also in infancy, it is not a typical species.

As for the lactoferrin peptides, it has been reported that some peptides purified from pepsin digestion product of bovine lactoferrin have antimicrobial activity (Non-patent document 5), and possibilities of them as preservatives of natural foods and antimicrobial agents used in the fields of drug and veterinary medicine have been suggested. However, it is not known that these peptides have a *bifidobacterium* proliferation promotion action.

As an agent for promoting proliferation of *Bifidobacterium breve*, N-acetylneuraminic acid and/or sialyllactose are known (Patent document 2). However, any peptide having a proliferation promotion effect for *Bifidobacterium infantis* and *Bifidobacterium breve* is not known.

PRIOR ART REFERENCES

Patent Documents

Patent document 1: Japanese Patent Laid-open (KOHYO) No. 2001-516570
Patent document 2: Japanese Patent Laid-open (KOKAI) No. 7-267866

Non-patent Documents

Non-patent document 1: Mitsuoka T., Journal of Intestinal Microbiology (Cyonai Saikingaku Zasshi), 19:179-192, 2005
Non-patent document 2: Rahman, M. M. et al., Int. J. Food Sci. Tech., 45:453-458, 2010
Non-patent document 3: Azuma, N. et al., Agric. Biol. Chem., 48:2159-2162, 1984
Non-patent document 4: Liepke, C. et al., Eur. J. Biochem., 269:712-718, 2002
Non-patent document 5: Dionysius, D. A. et al., J. Dairy Sci., 80:667-674, 1997

SUMMARY OF THE INVENTION

Object to Be Achieved by the Invention

As described above, although milk protein-derived peptides having proliferation promoting action for *Bifidobacterium bifidum* are known, milk protein-derived peptides having a proliferation promoting action for *Bifidobacterium infantis* and/or *Bifidobacterium breve* that are important in infancy are not known.

An object of the present invention is to provide an agent for promoting proliferation of *Bifidobacterium infantis* and/or *Bifidobacterium breve*, which comprises a peptide derived from a milk protein as an active ingredient.

Means for Achieving the Object

The inventor of the present invention conducted various researches in order to achieve the aforementioned object. As a result, the inventor of the present invention found that one of the peptides reported as antimicrobial peptides (J. Dairy Sci., 80:667-674, 1997) and similar peptides had a proliferation promoting action for *bifidobacteria*, especially *Bifidobacterium infantis* and *Bifidobacterium breve*, and accomplished the present invention.

The present invention thus provides an agent for promoting proliferation of one or more bacterium selected from the group consisting of *Bifidobacterium infantis* and *Bifidobacterium breve*, which comprises a peptide dimer as an active ingredient, wherein: the peptide dimer comprises a peptide consisting of the amino acid sequence of SEQ ID NO: 1 and a peptide consisting of any one of the amino acid sequences of SEQ ID NOS: 2 to 4, wherein the peptide consisting of the amino acid sequence of SEQ ID NO: 1 and the peptide consisting of any one of the amino acid sequences of SEQ ID NOS: 2 to 4 are bound through a disulfide bond between a cysteine residue of each peptide.

The present invention also provides a composition for promoting proliferation of one or more bacterium selected from the group consisting of *Bifidobacterium infantis* and *Bifidobacterium breve*, which comprises the aforementioned agent and one or more bacterium selected from the group consisting of *Bifidobacterium infantis* and *Bifidobacterium breve*.

According to a preferred embodiment of the composition of the present invention, the composition is a drug.

According to another preferred embodiment of the composition of the present invention, the composition is a food or drink.

The present invention further provides use of a peptide for promoting proliferation of one or more bacterium selected from the group consisting of *Bifidobacterium infantis* and *Bifidobacterium breve*, wherein:

the peptide is a peptide dimer comprising a peptide consisting of the amino acid sequence of SEQ ID NO: 1 and a peptide consisting of any one of the amino acid sequences of SEQ ID NOS: 2 to 4, wherein the peptide consisting of the amino acid sequence of SEQ ID NO: 1 and the peptide consisting of any one of the amino acid sequences of SEQ ID NOS: 2 to 4 are bound through a disulfide bond between a cysteine residue of each peptide.

The present invention also provides a method for promoting proliferation of one or more bacterium selected from the group consisting of *Bifidobacterium infantis* and *Bifidobacterium breve* in an animal, comprising:

administering a peptide to the animal, wherein the peptide is a peptide dimer comprising a peptide consisting of the amino acid sequence of SEQ ID NO: 1 and a peptide consisting of any one of the amino acid sequences of SEQ ID NOS: 2 to 4, wherein the peptide consisting of the amino acid sequence of SEQ ID NO: 1 and the peptide consisting of any one of the amino acid sequences of SEQ ID NOS: 2 to 4 are bound through a disulfide bond between a cysteine residue of each peptide.

Embodiments for Carrying out the Invention

Hereafter, preferred embodiments of the present invention will be explained in detail. However, the present invention is not limited to the following preferred embodiments, and can be freely modified within the scope of the present invention. The percentages mentioned in this specification are used on mass basis, unless specifically indicated.

The peptide as the active ingredient of the proliferation promoting agent of the present invention is a peptide dimer comprising a peptide consisting of the amino acid sequence of SEQ ID NO: 1 and a peptide consisting of any one of the amino acid sequences of SEQ ID NOS: 2 to 4, wherein the peptide consisting of the amino acid sequence of SEQ ID NO: 1 and the peptide consisting of any one of the amino acid sequences of SEQ ID NOS: 2 to 4 are bound through a disulfide bond between a cysteine residue of each peptide. Structures of the peptide dimer are shown by the following formulas (1) to (3). The amino acid sequences of the upper and lower peptides of the formula (1) correspond to the amino acid sequences of SEQ ID NOS: 1 and 2, respectively. The amino acid sequences of the upper and lower peptides of the formula (2) correspond to the amino acid sequences of SEQ ID NOS: 1 and 3, respectively. The amino acid sequences of the upper and lower peptides of the formula (3) correspond to the amino acid sequences of SEQ ID NOS: 1 and 4, respectively. In this specification, these peptide dimers are also referred to as "active peptide". The active peptide may be a salt of the aforementioned peptide dimers.

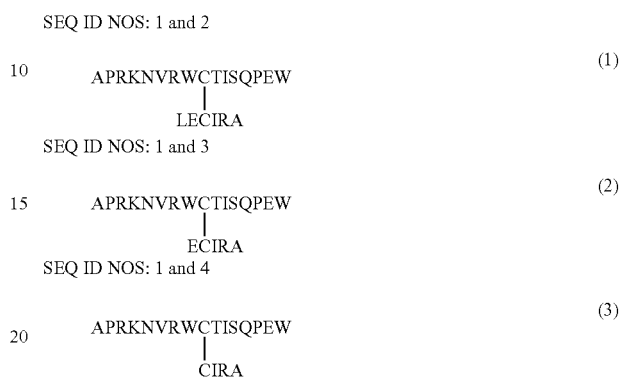

The active peptide has a *bifidobacterium* proliferation promoting action, and especially, it selectively shows a marked proliferation promoting action for *Bifidobacterium infantis* and *Bifidobacterium breve*. The "proliferation promoting action" of the active peptide refers to an action for providing an increased number of intestinal *Bifidobacterium infantis* and/or *Bifidobacterium breve* when the active peptide is ingested by an animal or human, as compared to that observable when the active peptide is not ingested by the animal or human, or an increased number of *Bifidobacterium infantis* or *Bifidobacterium breve* when the bacterium is cultured in a medium containing the active peptide, as compared to that observable when the bacterium is cultured in a medium not containing the active peptide.

The active peptide shows a homology of about 50% with respect to the structure of the peptide represented by the following formula (4), which is derived from human lactoferrin and known to have a proliferation promoting action for *Bifidobacterium bifidum* (Liepke, C. et al., Eur. J. Biochem., 269:712-718, 2002), but the activity spectra of them are completely different from each other. That is, the active peptide shows an extremely strong proliferation promoting action for *Bifidobacterium infantis* and *Bifidobacterium breve* as compared to bovine lactoferrin or the human lactoferrin-derived peptide represented by the formula (4), whereas the active peptide scarcely shows proliferation promoting action for *Bifidobacterium bifidum*, unlike bovine lactoferrin or the human lactoferrin-derived peptide of the formula (4). The amino acid sequence of the human lactoferrin-derived peptide of the formula (4) is shown as SEQ ID NO: 5.

SEQ ID NO: 5

(4)

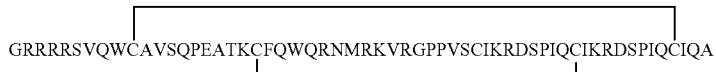

The active peptide can be prepared by chemically synthesizing each of the peptide monomers that constitutes the active peptide, and binding those peptides with a disulfide bond. The chemical synthesis of the peptides can be performed by the liquid phase method or solid phase method usually used for the synthesis of oligopeptides. Deprotection of the synthesized peptides is carried out as required, and unreacted reagents, by-products, and so forth are removed. Such peptide synthesis can be performed by using a commercial peptide synthesizer. Target peptides are preferably isolated and purified from the aforementioned synthesis product (mixture). Purification of peptides can be performed by methods similar to those usually used for purification of oligopeptides, for example, appropriate combinations of various chromatography techniques such as ion exchange chromatography, adsorption chromatography, reverse phase chromatography, partition chromatography and gel filtration chromatography, solvent precipitation, salting out, distribution between two kinds of liquid phases, and so forth. When the peptides are purified, whether a fraction contains the target peptides can be determined by binding peptides in the fraction with a disulfide bond, and determining proliferation promoting action of the obtained dimer for *Bifidobacterium infantis* or *Bifidobacterium breve* as an index using the method described in the examples, and the active ingredient in the fraction can be identified by mass spectrometry or/and by using a protein sequencer.

Further, the peptide monomers, which constitute the active peptide, can also be prepared by expressing recombinant DNAs coding for the peptides in an appropriate host cell. As the vector required for the preparation of the recombinant DNAs and the host, those usually used for preparation of proteins or peptides can be used.

In order to bind the peptide monomers through a disulfide bond, for example, a mixture of the peptide monomers can be placed under an appropriate oxidation condition. Such an appropriate oxidation condition can be realized by mixing a reducing agent such as dithiothreitol, reduced glutathione, or cystine, and an oxidant such as oxidized glutathione or cysteine in an appropriate ratio. Since the dimers formed by binding through a disulfide bond contains heterodimers and homodimers, it is preferable to isolate and purify a heterodimer having the structure of the formula (1), (2), or (3). The target heterodimer can be isolated and purified by the various chromatography techniques described above and so forth.

The active peptide can be used as the agent for promoting proliferation of *Bifidobacterium infantis* and/or *Bifidobacterium breve* (henceforth also referred to as the "agent of the present invention") as it is or as a combination with pharmaceutically acceptable additive(s). One kind of the active peptide can be independently used, and two or more kinds of the active peptides can be used as a mixture.

Preparation form of the agent of the present invention is not particularly limited, and examples include tablets (including sugar-coated tablets, enteric coated tablets, and buccal tablets), powders, capsules (including enteric capsules and soft capsules), granules (including coated granules), pills, troches, liposome-encapsulated agents, solutions, pharmaceutically acceptable sustained release preparations of these, and so forth. When the preparation is prepared, additives commonly used in usual oral drugs used as pharmaceutical carriers, such as excipient, binder, disintegrating agent, lubricant, stabilizer, corrigent, diluent, surfactant and solvent, can be used. Further, so long as the effect of the present invention is not impared, the active peptide may be used together with an agent or pharmaceutical composition having a proliferation promoting action for *Bifidobacterium infantis* and/or *Bifidobacterium breve*, which is already known or will be found in future. The pharmaceutical composition used together may be contained in the agent of the present invention as one of active ingredients, or may not be contained in the agent of the present invention, but combined as a separate drug with the agent of the present invention to form a commercial product.

Examples of the carrier and excipient used for the aforementioned preparation include lactose, glucose, sucrose, mannitol, potato starch, corn starch, calcium carbonate, calcium phosphate, calcium sulfate, crystalline cellulose, powdered glycyrrhiza, powdered gentiana, and so forth, and examples of the binder include, for example, starch, gelatin, syrup, polyvinyl alcohol, polyvinyl ether, polyvinylpyrrolidone, hydroxypropylcellulose, ethylcellulose, methylcellulose, carboxymethylcellulose, and so forth.

Examples of the disintegrating agent include starch, agar, gelatin powder, carboxymethylcellulose sodium, carboxymethylcellulose calcium, crystalline cellulose, calcium carbonate, sodium hydrogencarbonate, sodium arginate, and so forth.

Examples of the lubricant include magnesium stearate, hydrogenated vegetable oil, Macrogol, and so forth, and examples of the colorant include Red No. 2, Yellow No. 4, Blue No. 1, which are allowed to be added to drugs, and so forth.

Tablets and granules can be coated with sucrose, hydroxypropylcellulose, purified shellac, gelatin, sorbitol, glycerol, ethylcellulose, hydroxypropylcellulose, hydroxypropylmethylcellulose, polyvinylpyrrolidone, cellulose acetate phthalate, hydroxypropylmethylcellulose phthalate, methyl methacrylate, methacrylic acid polymer, and so forth, as required.

One embodiment of the present invention is use of the active peptide in preparation of an agent for promoting proliferation of *Bifidobacterium infantis* and/or *Bifidobacterium breve*. Another embodiment of the present invention is the active peptide used for promotion of proliferation of *Bifidobacterium infantis* and/or *Bifidobacterium breve*. Still another embodiment of the present invention is use of the active peptide for promoting proliferation of *Bifidobacterium infantis* and/or *Bifidobacterium breve*.

A further embodiment of the present invention is a method for promoting proliferation of *Bifidobacterium infantis* and/or *Bifidobacterium breve* in an animal or human, which comprises administering the active peptide to the animal or human. Examples of the animal include, bovine, goat, sheep, and so forth. Human and bovine are especially preferred.

Although content of the active peptide contained in the agent of the present invention is not particularly limited, and may be appropriately chosen, it is, for example, 0.001 to 10 mass %, preferably 0.01 to 3 mass %, particularly preferably 0.1 to 1 mass %, of the preparation of the agent. When the agent of the present invention contains two or more kinds of the active peptides, the content of the peptide is the total content of the peptides.

The agent of the present invention is useful for improvement of intestinal bacterial flora, immune control, prophylaxis or treatment of diarrhea, constipation, obesity, inflammatory bowel disease, and so forth.

Although administration time of the agent of the present invention is not particularly limited, and can be appropriately chosen according to conditions of the object of the administration, it may be administered at a frequency of, for example, once/3 days to 5 times/day. Dose of the agent of the present invention is appropriately chosen depending on age, sex, state of the object of administration, other conditions, and so forth, and for example, dosage of administration is preferably chosen from the range of 10 to 5000 µg/kg/dose, more preferably 50 to 500 µg/kg/dose, as a standard in terms of the amount of the active peptide (when the active peptide consists of two or more kinds of peptides, it is the total amount of the peptides).

The object of the administration is preferably human, and infant is especially preferred. Further, when *Bifidobacterium infantis* and/or *Bifidobacterium breve* is not dominant in the intestinal bacterial flora of the object of the administration, for example, when the object of the administration is a person other than infant, it is preferable to administer *Bifidobacterium infantis* and/or *Bifidobacterium breve* together with the active peptide. Both the active peptide and *Bifidobacterium infantis* and/or *Bifidobacterium breve* may be contained in the agent of the present invention, or separate preparations containing them may be combined. Although amount of *Bifidobacterium infantis* and/or *Bifidobacterium breve* relative to the active peptide in the agent is not particularly limited, it is preferably 10 to $10^5$ CFU (colony forming unit)/µg of the active peptide, more preferably $10^2$ to $10^4$ CFU/µg of the active peptide.

The agent of the present invention, or the active peptide as the active ingredient of the agent may be contained in diets (drinks and foods). The active peptide or the agent of the present invention may be contained in a food or drink as an active ingredient to prepare a food or drink having a proliferation promoting action for *Bifidobacterium infantis* and/or *Bifidobacterium breve*, as one embodiment of the agent for promoting proliferation of *Bifidobacterium infantis* and/or *Bifidobacterium breve*.

Forms and properties of the foods and drinks are not particularly limited so long as the effect of the active peptide is not degraded, and they can be orally ingested, and they can be prepared by using raw materials used for usual foods and drinks and usual methods, except that the active peptide is added.

Forms of the foods are not particularly limited, and they may be in the form of liquid, paste, solid, powder, or the like. Examples include, for example, tablet confectioneries, and liquid diets, as well as flour products such as bread, macaroni, spaghetti, noodles, cake mix, fry powder and bread crumbs; ready-to-eat foods such as instant noodles, cup noodles, retort and cooked foods, canned cooking, foods for microwave heating, instant soup and stew, instant miso soup and Japanese clear soup, canned soup, freeze-dried foods, and other ready-to-eat foods; processed agricultural products such as canned agricultural products, canned fruits, jams and marmalades, pickles, cooked beans, dry agricultural products, and cereals (processed grain products); processed marine products such as canned marine products, fish ham and sausages, seafood paste products, marine dainties, and tsukudani (marine products boiled in soy sauce); processed livestock products such as canned livestock products and pastes, and livestock meat ham and sausages; milks and dairy products such as processed milk, milk drinks, yoghurts, lactic acid bacteria beverages, cheese, ice creams, modified milk powders, creams, and other dairy products; oils and fats such as butter, margarines, and vegetable oils; basic seasoning such as soy sauce, miso, sauces, processed tomato seasoning, mirin, and vinegars; complex seasonings and foods such as processed and pre-cooked foods, curry powder or roux, sauces for dipping, dressings, noodle soups, spices, and other complex seasonings; frozen foods such as frozen food materials, semi-cooked frozen foods, and cooked frozen foods; confectioneries such as caramel candies, candies, chewing gums, chocolates, cookies, biscuits, cakes, pies, snacks, crackers, Japanese sweets, rice confectioneries, bean confectioneries, dessert pastries, and other confectioneries; beverages such as carbonated drinks, natural fruit juices, fruit juice drinks, fruit juice soft drinks, fruit pulp drinks, fruit drinks with fruit pulp, vegetable based drinks, soy milk, soy milk drinks, coffee drinks, tea drinks, powdered drinks, concentrated drinks, sports drinks, energy drinks, alcoholic drinks, and other beverages; other commercial foods such as baby foods, rice seasonings, and seaweed seasonings for boiled rice soaked with tea; modified milk powder for infants; enteral nutritions; functional foods (foods for specified health use, foods with nutrient function claims), and so forth.

Furthermore, by adding the active peptide or the agent of the present invention to a feed as an active ingredient, a feed having a *bifidobacterium* proliferation promoting action can be prepared, as one embodiment of the agent for promoting proliferation of *bifidobacterium*.

Form of the feed is not particularly limited. For example, the feed can be prepared by blending cereals such as corn, wheat, barley, rye and milo; vegetable oil meals such as soybean oil meal, rapeseed oil meal, coconut oil meal and linseed oil meal; brans such as wheat bran, rice bran, and defatted rice bran; production meals such as cone gluten meal and corn jam meal; animal or fish-derived feeds such as fish meal, skim milk powder, whey, yellow grease and tallow; yeasts such as torula yeast and brewer's yeast; mineral material feeds such as calcium phosphate and calcium carbonate; oils and fats; simple substance amino acids; saccharides, and so forth. Examples of the form of the feed include, for example, pet food, livestock feed, fish breeding feed, and so forth.

Although amount of the active peptide contained in the food or drink (including feed) of the present invention is not particularly limited, and it may be appropriately chosen, it may be, for example, 0.00001 to 1 mass %, preferably 0.0001 to 0.1 mass %, particularly preferably 0.001 to 0.01 mass %, in terms of the amount of the active peptide (when the active peptide consists of two or more kinds of peptides, it is the total amount of the peptides) in the food or drink.

It is also preferred that the food or drink contains *Bifidobacterium infantis* and/or *Bifidobacterium breve* together with the active peptide. Amount of *Bifidobacterium infantis* and/or *Bifidobacterium breve* relative to the active peptide may be similar to that described for the agent of the present invention.

EXAMPLES

Hereafter, the present invention will be more specifically explained with reference to examples. However, the present invention is not limited to these examples.

Example 1

Chemical syntheses of the peptide of the present invention having the structure of the formula (1) (henceforth also referred to as "Active peptide 1"), and the peptide derived from human lactoferrin of the formula (4) (henceforth also referred to as "human lactoferrin peptide") were entrusted to Toray Research Center Inc. Purities of the synthesized peptides were higher than 95%. As bovine lactoferrin, bovine lactoferrin prepared by the method described in Japanese Patent Laid-open (KOKAI) No. 63-152400, Example 8 (purity was higher than 96%) was used.

A 9.375 µM aqueous solution of each peptide was adjusted to pH 6.5 with an HCl aqueous solution, and subjected to filtration sterilization using a 0.22-µm membrane. Each peptide solution was diluted with dilution water to obtain 9.375 µM, 3.125 µM, 0.9375 µM, and 0.3125 µM sample solutions. As the dilution water, purified water adjusted to pH 6.5 with an HCl solution and sterilized at 115° C. for 15 minutes was used.

Bifidobacterium proliferation promoting activities of the aforementioned peptides were evaluated as follows.

The bifidobacteria used for the experiment were as follows. These strains can be obtained from ATCC (American Type Culture Collection, http://www.atcc.org/).

Bifidobacterium infantis ATCC 15697$^T$
Bifidobacterium breve ATCC 15700$^T$
Bifidobacterium bifidum ATCC 29521$^T$ A cell suspension of each strain (100 µL) cryopreserved in a 10% skim milk medium was added to the MRS liquid medium (3 mL), and culture was performed at 37° C. for 16 hours under an anaerobic condition. The culture medium (100 µL) was added to the MRS liquid medium (3 mL). The MRS liquid medium was prepared by dissolving Difco Lactobacilli MRS Broth (5.5 g, BD, "Difco" is a registered trademark of Difco Laboratories, Incorporated), and L-cysteine monohydrochloride monohydrate (50 mg, Wako Pure Chemical Industries, Co., Ltd.) in pure water so as to obtain a final volume of 100 mL, adjusting the solution to pH 6.5 with an HCl aqueous solution, and sterilizing the solution at 115° C. for 15 minutes. Further, a concentrated medium containing the components at twofold concentrations was prepared in the same manner as described above, except that Difco Lactobacilli MRS Broth and L-cysteine monohydrochloride monohydrate were used in amounts of 11 g and 100 mg, respectively.

The aforementioned culture medium was diluted with the MRS liquid medium so as to obtain a turbidity of 0.8 measured at a wavelength of 630 nm. This diluted culture medium was further diluted 100 times with the MRS liquid medium. The obtained diluted culture medium is referred to as 1% diluted culture medium.

Anaerobic culture was performed at 37° C. for 16 hours in a mixture of 100 µL of the twofold concentrated culture medium, 80 µL of a sample solution or the dilution water, and 20 µL of the 1% diluted culture medium (inoculation volume was 0.1%) or the MRS liquid medium (inoculation volume was 0%) on a 96-well plate (FALCON 353072). The final concentration of the peptide in the mixture was 3.75 µM, 1.25 µM, 0.375 µM, 0.125 µM, or 0 µM.

After the culture, turbidity of each culture medium was measured at a wavelength of 630 nm, and the proliferation promoting ratio (%) was calculated in accordance with the following equation.

$$\text{Proliferation promoting ratio (\%)} = (OD_{S1} - OD_{S0})/(OD_{C1} - OD_{C0}) \times 100 - 100$$

$OD_{S1}$: Turbidity observed after culture performed at a sample concentration of 3.75 to 0.125 µM and inoculation volume of 0.1% for 16 hours $OD_{S0}$: Turbidity observed after culture performed at a sample concentration of 3.75 to 0.125 µM and inoculation volume of 0% for 16 hours $OD_{C1}$: Turbidity observed after culture performed at a sample concentration of 0 µM and inoculation volume of 0.1% for 16 hours $OD_{C0}$: Turbidity observed after culture performed at a sample concentration of 0 µM and inoculation volume of 0% for 16 hours The results are shown in Table 1.

TABLE 1

| | Proliferation promoting ratio (%) | | | | | | | | | | | |
|---|---|---|---|---|---|---|---|---|---|---|---|---|
| | Active peptide 1 (µM) | | | | Bovine lactoferrin (µM) | | | | Human lactoferrin peptide (µM) | | | |
| | 0.125 | 0.375 | 1.25 | 3.75 | 0.125 | 0.375 | 1.25 | 3.75 | 0.125 | 0.375 | 1.25 | 3.75 |
| B. infantis ATCC 15697 | 15 | 21 | 36 | 206 | 1 | 1 | 13 | 23 | 0 | 2 | 10 | 39 |
| B. breve ATCC 15700 | 28 | 80 | 116 | 512 | 2 | 4 | 8 | 21 | 0 | 1 | 12 | 30 |
| B. bifidum ATCC 29521 | 0 | -2 | 0 | -1 | 8 | 8 | 10 | 12 | 3 | 6 | 9 | 14 |

Active peptide 1 of the present invention showed a markedly higher proliferation promoting effect for *Bifidobacterium infantis* and *Bifidobacterium breve* as compared to the bovine lactoferrin and the human lactoferrin peptide.

However, Active peptide 1 did not show proliferation promoting effect for *Bifidobacterium bifidum*.

The bovine lactoferrin has a molecular weight of about 80,000, and the human lactoferrin peptide has a molecular weight of 5757.7, but Active peptide 1 has a molecular weight of 2673.1 (about 1/30 and about 1/2 of the foregoing peptides, respectively). Therefore, Active peptide 1 is expected to show high effect with a smaller amount.

Example 2

Chemical syntheses of the peptides of the present invention having the structures of the formula (2) (henceforth also referred to as "Active peptide 2") and the formula (3) (henceforth also referred to as "Active peptide 3") were entrusted to Toray Research Center Inc.

Bifidobacterium proliferation promoting activities of the aforementioned peptides were evaluated in the same manner as that of Example 1. The results are shown in Table 2.

TABLE 2

| | Proliferation promoting ratio (%) | | | | | | | |
|---|---|---|---|---|---|---|---|---|
| | Active peptide 2 (μM) | | | | Active peptide 3 (μM) | | | |
| | 0.125 | 0.375 | 1.25 | 3.75 | 0.125 | 0.375 | 1.25 | 3.75 |
| B. infantis ATCC 15697 | 0 | 12 | 48 | 174 | 9 | 18 | 73 | 238 |
| B. breve ATCC 15700 | 5 | 31 | 87 | 139 | 7 | 37 | 85 | 127 |
| B. bifidum ATCC 29521 | −4 | −2 | 0 | −1 | −1 | −2 | −3 | −4 |

Both Active peptides 2 and 3 of the present invention showed a marked proliferation promoting effect for *Bifidobacterium infantis* and *Bifidobacterium breve*.

INDUSTRIAL APPLICABILITY

Since the proliferation promoting agent of the present invention has a proliferation promoting action for *Bifidobacterium infantis* and *Bifidobacterium breve*, ingestion of the agent can provides an intestinal environment in which these bacteria are dominant. The peptide as the active ingredient of the proliferation promoting agent of the present invention is derived from a milk protein, and therefore it is expected to be safe.

Further, even in the case of a person other than infants, a composition containing the proliferation promoting agent of the present invention and *Bifidobacterium infantis* and/or *Bifidobacterium breve* can be ingested in a state that the functions of the bacteria are enhanced, and therefore it is useful as a drug, food, drink, or the like.

What is claimed is:

1. A composition comprising a peptide dimer and 10 to $10^5$ CFU of one or more bacterium selected from the group consisting of *Bifidobacterium infantis* and *Bifidobacterium breve* per 1 μg of the peptide dimer, wherein:

the peptide dimer comprises a peptide consisting of the amino acid sequence of SEQ ID NO: 1, and a peptide consisting of the amino acid sequence of SEQ ID NO: 2, and wherein the peptide consisting of the amino acid sequence of SEQ ID NO: 1 and the peptide consisting of the amino acid sequences of SEQ ID NO: 2 are bound through a disulfide bond between a cysteine residue of each peptide.

2. The composition according to claim 1, wherein the composition is a drug.

3. The composition according to claim 1, wherein the composition is a food or drink.

4. A method for improving intestinal bacterial flora, and treating diarrhea, constipation, obesity, or inflammatory bowel disease, comprising:

administering the composition according to claim 1 to an animal or a human in need thereof.

5. The method according to claim 4, wherein the dosage of administration of the composition is the range of 10 to 5000μg/kg/dose in terms of the amount of the peptide dimer at a frequency of once/3 days to 5 times/day.

* * * * *